United States Patent [19]

Welt et al.

[11] Patent Number: 5,160,723
[45] Date of Patent: Nov. 3, 1992

[54] METHOD OF IMAGING COLORECTAL CARCINOMA LESION AND COMPOSITION FOR USE THEREIN

[75] Inventors: Sydney Welt; Chaitanya R. Divgi; Samual Yeh; Lloyd J. Old, all of New York, N.Y.; Herbert F. Oettgen, New Canaan, Conn.; Francisco X. Real, Barcelona, Spain; Junichi Sakamoto, Chikusaku Nagoya, Japan

[73] Assignee: Sloan-Kettering Institute For Cancer Research, New York, N.Y.

[21] Appl. No.: 671,132

[22] Filed: Mar. 18, 1991

Related U.S. Application Data

[60] Division of Ser. No. 327,765, Mar. 23, 1989, abandoned, and a continuation-in-part of Ser. No. 118,411, Nov. 6, 1987, abandoned, which is a continuation of Ser. No. 724,991, Apr. 19, 1985, abandoned.

[51] Int. Cl.$^5$ ............... A61K 49/02; C07K 15/28; C07K 15/00
[52] U.S. Cl. ............... 424/1.1; 530/388.8; 530/808; 530/809; 530/391.3; 530/866; 424/85.8; 436/501; 436/548; 436/808; 436/813; 435/240.27; 935/95; 935/103; 935/106; 935/110
[58] Field of Search ............... 436/501, 512, 548, 808, 436/813; 530/387, 808, 809, 388.8, 391.3; 424/1.1, 85.8, 85.91; 435/240.27; 935/95, 103, 106, 110

[56] References Cited

U.S. PATENT DOCUMENTS

| | | | |
|---|---|---|---|
| 4,471,057 | 9/1984 | Koprowski et al. | 436/518 |
| 4,579,827 | 4/1986 | Sakamoto et al. | 436/536 |
| 4,818,682 | 4/1989 | Linnane | 436/813 X |
| 4,857,452 | 8/1989 | Ho | 436/813 X |
| 4,892,933 | 1/1990 | Salem et al. | 530/387 |
| 4,904,596 | 2/1990 | Hakamori | 530/387 X |
| 4,916,213 | 4/1990 | Scannon et al. | 530/387 X |
| 5,051,355 | 9/1991 | Yoshida et al. | 530/387 X |

OTHER PUBLICATIONS

Koprowski et al., *Science*, vol. 212, pp. 53–55, "Specific Antigen . . . " (Apr. 1981).
Magnani et al., *Science*, vol. 212, pp. 55–56, "A Monosialoganglioside . . . " (Apr. 1981).
Pimm, M. V. et al., *Behring Inst. Mitt.*, No. 74, pp. 80–86, May 1984.

*Primary Examiner*—Robert L. Stoll
*Assistant Examiner*—John M. Covert
*Attorney, Agent, or Firm*—John P. White

[57] ABSTRACT

This invention provides a method of imaging a colorectal carcinoma lesion in a human patient which comprises administering to the patient a monoclonal antibody capable of binding to a cell surface antigen associated with the coloretal carcinoma lesion and which is labeled with an imaging agent under conditions so as to form a complex between the monoclonal antibody and the cell surface antigen, imaging any complex so formed, and thereby imaging the colorectal carcinoma lesion.

This invention also provides a monoclonal antibody designated AS 33 (ATCC Accession No. HB 8779) and the hybridoma which produces it.

8 Claims, 11 Drawing Sheets mAb A33 - patient 11

| CELLS | A33 |
|---|---|
| COLON CARCINOMA | |
| HT-29,SW-480,SW-403 | ◐ ◐ ● |
| SW-48,CACO-2,SW-1116 | ○ ○ ● |
| SK-CO-10,SK-CO-13 | ○ ○ ○ |
| SW-1417,SW-1222,SK-CO-15 | ○ ◐ ○ |
| SW-620,SW-837,SK-CO-11 | ○ ● ● |
| SW-1083,SK-CO-12,SK-CO-1 | ○ ○ ○ |
| PANCREAS CARCINOMA | |
| ASPC-1,CAPAN-1,CAPAN-2 | ● ○ ○ |
| HEPATIC AND BILIARY CARCINOMA | |
| SK-HEP-1,SK-CHL-1 | ○ ○ ○ |
| LUNG CARCINOMA | |
| CALU-1, CALU-5, CALU-6 | ○ ○ ○ |
| SK-MES-1, CK-LU-1, SK-LC-LL | ○ ○ ○ |
| SK-LC-1,-2,-4 | ○ ○ ○ |
| SK-LC-5,-6,-8 | ○ ○ ○ |
| SK-LC-9,-10,-12 | ○ ○ ○ |
| SK-LC-15,-16,-17 | ○ ○ ○ |
| SK-LC-18,-19.-23 | ○ ○ ○ |
| SK-LC-24,-25,-28 | ○ ○ ○ |
| BLADDER CARCINOMA | |
| 253-J,SW-780,TCC-SUP | ○ ○ ○ |
| 5637,VM-CUB-1,VM-CUB-2 | ○ ○ ○ |
| VM-CUB-3,575-A,RT-4 | ○ ○ ○ |
| 639-V,J-82 | ○ ○ |
| BREAST CARCINOMA | |
| MDA-MB-361,MCF-7,CAMA | ○ ○ ○ |
| SK-BR-3,MDA-MB-157,ALAB | ○ ○ ○ |
| MDA-MB-231,BT-20,SK-BR-7 | ○ ○ ○ |

Figure 1B

| CELLS | A33 |
|---|---|
| OVARIAN CARCINOMA | |
| SK-OV-4,SK-OV-6,A-7 | O O O |
| SW-626 | O |
| KIDNEY CARCINOMA | |
| SK-RC-1,-2,-4 | O O O |
| SK-RC-7,-9,-10 | O O O |
| SK-RC-17,-18,-21 | O O O |
| SK-RC-26A,-26B,-28 | O O O |
| SK-RC-29,-35,-37 | O O O |
| SK-RC-39,-42,-44 | O O O |
| SK-RC-45,-48 | O O |
| TERATOCARCINOMA | |
| 577MF,Tera-1,833KE | O O O |
| CHORIOCARCINOMA | |
| GCO-SV(O),OCC-M/M | O O |
| MELANOMA | |
| VM-88,MeWo,SK-MEL-13 | O O O |
| SK-MEL-23,-27,-28 | O O O |
| SK-MEL-29,-33,-37 | O O O |
| SK-MEL-42,-64,-73 | O O O |
| SK-MEL-90,-129,-133 | O O O |
| SK-MEL-176 | O |
| ASTROCYTOMA | |
| SK-MG-1,-2,-3 | O O O |
| SK-MG-4,-9,-10 | O O O |
| SK-MG-12,-13,-14 | O O O |
| SK-MG-16,MS,U-343 | O O O |
| A-582 | O |
| NEUROBLASTOMA | |
| MC-MB-1,SMS-KAN,SK-N-MC | O O O |
| SMS-SAN,SK-N-BE(2) | O O |

Figure 1C

| CELLS | A33 |
|---|---|
| LEUKEMIA (B cell) | |
| ARH 77-AG, ARA-10,DAUDI | O O O |
| SK-LY-16,-18,BALL-1 | O O O |
| SK-DHL-2,SKO-007,RAJI | O O O |
| LICR-LON-HMy2,UC 729-6 | O O |
| LEUKEMIA (NULL Cell) | |
| NALM-1,NALM-16,NKL-1 | O O O |
| NKL-2,NALL-1 | O O |
| LEUKEMIA (T Cell) | |
| HPR-ALL,T-45,MOLT-4 | O O O |
| CCRF-HSB-2,CCRF-CEM,P-12 | ◐ ◐ ● |
| LEUKEMIA (Myelomonocytic) | |
| HL60,K-562,KG-1-G | O O O |
| NORMAL FIBROBLAST | |
| #1,#2,#3 | O O O |
| #4,#5,#6 | O O O |
| #7,#8 | O O |
| NORMAL KIDNEY EPITHELIUM | |
| #1,#2 | O O |

Each symbol represents reults of testing of one antibody with each individual cell line. Antibody titer is defined as the highest dilution at which 50% of target cells form rosettes.

Serological assay- mixed hemadsorption. ●, $1 \times 10^{-3} - 1 \times 10^{-6}$ ; ◐, $< 1 \times 10^{-3}$ ; ⊖, negative in direct tests, positive in absorption tests;

O, no reactivity at an antibody dilution of $10^{-2}$

Figure 2A

Reactivity of Mouse Monoclonal Antibodies with Frozen Sections of Normal Human Fetal (F)* and Adult (A) Tissues. Serological Assay: Indirect Immunofluorescence

| TISSUE | MONOCLONAL ANTIBODY ||||
|---|---|---|---|---|
| | F A | F A | F A | F A |
| Colon | | O ● | | |
| Small Intestine | | O O | | |
| Stomach | | O O | | |
| Esophagus | | O O | | |
| Pancreas: Endocrine | | O O | | |
|     Exocrine | | O O | | |
| Liver: Hepatocytes | | O O | | |
|     Biliary Epithelium | | O O | | |
| Lung: Bronchial Epithelium | | O O | | |
|     Pneumocytes | | O O | | |
| Urothelium | | O O | | |
| Prostate | | O O | | |
| Kidney: Glomerus | | O O | | |
|     Proximal Tubules | | O O | | |
|     Henle's Loop | | O O | | |
|     Distal Tubules | | O O | | |
|     Collecting Tubules | | O O | | |
| Testis: Germ Cells | | O O | | |
|     Endocrine Cells | | O O | | |
| Ovary | | O O | | |
| Placenta: Syncytrophoblast | | O O | | |
|     Cytotrophoblast | | O O | | |
| Uterus: Endometrium | | O O | | |
|     Myometrium | | O O | | |
| Cervix: Endocervix | | O O | | |
|     Exocervix | | O O | | |
| Breast: Duct Cells | | O ◐ | | |
|     Acinar Cells | | O ◐ | | |
| Adrenal | | O O | | |
| Skin: Epidermis | | O O | | |
|     Adnexa | | O O | | |
|     Melanocytes | | O O | | |

Figure 2B

|  | A33 |
|---|---|
| TISSUE | F A |
| Brain: Neurons | O O |
| Glial Cells | O O |
| Dendrites | O O |
| Thyroid | O O |
| Spleen: White Pulp | O O |
| Red Pulp | O O |
| Lymph Nodes | O O |
| Thymus | O O |
| Heart | O O |
| Muscle | O O |
| Endothelial Cells | O O |
| Fibroblasts | O O |
| Cartilage | O O |
| Interstitial Matrix | O O |
| Secretions | O O |

Reactivity of monoclonal antibodies with tissue sections is symbolized
the following way: O, no reactivity: ●, reactivity; ◐, heterogenous pattern of staining.

*Fetal tissues were obtained from a 14-week-old fetus.

Figure 3A mAb A33: TISSUE AND BLOOD DOSIME (DAY 7-8)

| PATIENT | Dose (mg) | | ID/gm X10⁻³ | Ab T/L | T/P | HSA T/L | T/P |
|---|---|---|---|---|---|---|---|
| 1 | 0.2 | | 1.1 | 2.7 | 0.57 | 0.23 | 0.12 |
| 2 | 0.2 | | 2.0 | 18.2 | 5.7 | 0.16 | 0.13 |
|   |     | | 1.4 | 12.9 | 4.1 |      |      |
|   |     | | 1.1 | 9.6  | 3.0 |      |      |
|   |     | | .8  | 6.8  | 2.1 |      |      |
|   |     | | .7  | 6.7  | 2.0 |      |      |
| 3 | 0.2 | | 4.0 | 23.8 | 9.6 | 0.14 | 0.25 |
|   |     | | 3.9 | 22.8 | 9.2 |      |      |
|   |     | | 1.8 | 10.3 | 4.2 |      |      |
|   |     | | 0.4 | 2.8  | 1.0 |      |      |
| 4 | 2.0 | | 1.0 | 25.0 | 5.3 | 0.18 | 0.05 |
|   |     | | 1.0 | 25.0 | 5.3 |      |      |
|   |     | | 0.8 | 20.0 | 4.2 |      |      |
| 5 | 2.0 | | 5.6 | 24.6 | 11.3 | 0.23 | 0.12 |
|   |     | | | 3.0 | 13.0 | 6.0 |      |      |
|   |     | | | 2.6 | 11.3 | 5.2 |      |      |
|   |     | | | 1.9 | 8.0  | 3.7 |      |      |
|   |     | (P)  | 1.8 | 7.7  | 3.6 |      |      |
|   |     | (LN) | 3.4 | 14.6 | 6.8 |      |      |
|   |     | (LN) | 2.7 | 11.8 | 5.5 |      |      |
|   |     | (LN) | 1.4 | 6.2  | 2.9 |      |      |
| 6 | 2.0 | | 2.3 | 15.6 | 4.6 | 0.58 | 0.15 |
|   |     | | 1.9 | 12.6 | 3.8 | 0.27 | 0.07 |
|   |     | | 0.5 | 3.6  | 1.0 |      |      |

Figure 3B

| PATIENT | Dose (mg) | ID/gm X10$^{-3}$ | Ab T/L | T/P | HSA T/L | T/P |
|---|---|---|---|---|---|---|
| 7 | 10.0 | 2.5 | 13.4 | 5.2 | 0.45 | 0.12 |
|   |      | 1.5 | 7.8  | 3.0 |      |      |
|   |      | 1.4 | 7.4  | 2.9 |      |      |
| 8 | 10.0 | 3.0 | 12.3 | 4.6 | 0.42 | 0.21 |
|   |      | 2.1 | 8.8  | 3.4 |      |      |
|   |      | 1.5 | 6.1  | 2.3 |      |      |
|   |      | 1.3 | 5.3  | 2.0 |      |      |
| 9 | 10.0 | 0.9 | 6.9  | 4.1 | 0.54 | 0.17 |
| 10 | 25.0 | 2.0 | 7.3 | 13.0 | 0.36 | 0.36 |
|   |      | 1.8 | 7.0  | 12.2 | 0.28 | 0.28 |
|   |      | 1.8 | 7.0  | 12.2 | 0.19 | 0.19 |
| 11 | 25.0 | 2.6 | 8.9 | 14.3 | 0.31 | 0.35 |
|   |      | 2.0 | 7.0  | 11.3 |      |      |
| 12 | 25.0 | 3.2 | 10.7 | 17.8 | 0.25 | 0.20 |
|   |      | 3.0 | 10.2 | 16.8 |      |      |
|   |      | 2.8 | 9.3  | 15.3 |      |      |
|   |      | 2.6 | 8.6  | 14.2 |      |      |
|   |      | 1.6 | 5.2  | 8.6  |      |      |

Figure 5
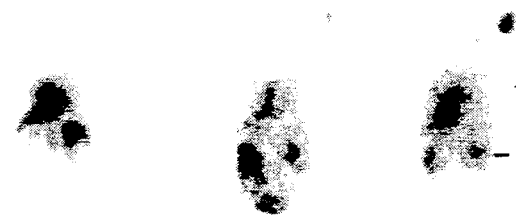

mAb A33 - patient 11

TUMOR/LIVER

|  | A33 | TA99 | 99mTc HSA |
|---|---|---|---|
| Lesion 1 | 93.4 | 2.1 | 0.4 |
|  | 100.7 | 4.9 | 0.4 |
|  | 70.1 | 5.4 | 0.5 |
|  | 78.8 | 3.8 | 0.6 |
| (Center) | 44.1 | 1.2 | 0.3 |
| Lesion 2 | 14.1 | 1.1 | 0.5 |
|  | 15.6 | 1.7 | 0.4 |
|  | 48.2 | 1.9 | 0.4 |
| (Center) | 12.0 | 1.1 | 0.3 |

TUMOR/PLASMA

|  | A33 | TA99 | 99mTc HSA |
|---|---|---|---|
| Lesion 1 | 23.4 | 0.6 | 0.5 |
|  | 25.2 | 1.4 | 0.7 |
|  | 17.5 | 1.5 | 0.8 |
|  | 19.7 | 1.1 | 0.4 |
| (Center) | 11.0 | 0.4 | 0.3 |
| Lesion 2 | 3.5 | 0.3 | 0.5 |
|  | 3.9 | 0.5 | 0.6 |
|  | 12.1 | 0.5 | 0.5 |
| (Center) | 3.0 | 0.3 | 0.4 |

METHOD OF IMAGING COLORECTAL CARCINOMA LESION AND COMPOSITION FOR USE THEREIN

This is a division of application Ser. No. 327,765, filed Mar. 23, 1989 now abandoned and is a continuation in part of U.S. Ser. No. 118,411 now abandoned, filed Nov. 6, 1987, which is a continuation of U.S. Ser. No. 724,991, filed Apr. 19, 1985 (now abandoned), the contents both of which are hereby incorporated by reference into the present application.

Throughout this application various publications are referenced by numbers within parentheses. Full citations for these publications may be found at the end of the specification immediately preceding the claims. The disclosures of these publications, in their entireties, are hereby incorporated by reference into this application in order to more fully describe the state of the art to which this invention pertains.

BACKGROUND OF THE INVENTION

In 1987, it is estimated that 145,000 cases of colon carcinoma will be diagnosed in the United States (1). Due to lack of effective systemic therapy for metastatic disease, 47% of all patients with colon cancer, and the majority of those with metastatic disease succumb to their malignancies (1). Thus far, chemotherapeutic agents have not exhibited sufficient antitumor activity to prolong the survival of patients with metastatic disease. Development of new diagnostic and therapeutic modalities is therefore of utmost importance.

The use of radioisotope labeled monoclonal antibodies as a diagnostic tool has been reported. Of the numerous monoclonal antibody studies which have been reported, the parameters defining specific tissue localization with radiolabeled monoclonal antibodies remain obscure. Detection of radioactivity over tumor sites by external scintigraphy does not always indicate specific localization (7). Mouse imaging experiments demonstrate that tissue vascularity and blood clearance of radiolabeled antibody strongly affect tissue antibody content (7). In a previous clinical trial of one antibody (8), tumor/nontumor radioactivity ratios were affected by several parameters including the time interval between antibody administration and biopsy as well as the types of normal tissue biopsied. Another issue is the antigen specificity of antibody localization. Isotype matched control antibodies are important to definitively prove that localization is specific.

These issues are addressed in this study by: 1) tissue biopsies from all patients seven days after administration of labeled antibody to document tumor and measure antibody uptake in tumor and normal (liver) tissues; 2) $^{99m}$Tc HSA scans were performed in all patients to show that radioactivity in tumors was not due to vascularity of tumors (blood flow studies); and 3) a control antibody was compared to AS 33 to demonstrate that $^{131}$I-AS 33 localization was specific.

SUMMARY OF THE INVENTION

This invention provides a method of imaging a colorectal carcinoma lesion in a human patient which comprises administering to the patient a monoclonal antibody capable of binding to a cell surface antigen associated with the colorectal carcinoma lesion and which is labeled with an imaging agent under conditions so as to form a complex between the monoclonal antibody and the cell surface antigen, imaging any complex so formed, and thereby imaging the colorectal carcinoma lesion.

This invention also provides a monoclonal antibody designated AS 33 (ATCC Accession No. HB 8779) and the hybridoma which produces it.

BRIEF DESCRIPTION OF THE FIGURES

FIGS. 1 (A-C) show the reactivity of monoclonal antibody AS 33 with a panel of tumor cell lines.

FIGS. 2 (A) and (B) illustrate the reactivity of monoclonal antibody AS 33 with frozen sections of normal human fetal and adult tissues.

FIGS. 3(A) and 3(B) summarizes tissue and blood dosimetry results for twelve patients who were administered radiolabeled AS 33.

FIG. 5 shows gamma camera imaging results at day 4 and day 6 using $^{131}$I labeled AS 33. A $^{99m}$TcHSA scan is shown in left panel which demonstrates a hypovascular lesion in the right lobe of the liver. $^{131}$I-AS 33 scans on day 4 and 6 show antibody localization in this hypovascular lesion. A surgical procedure performed several weeks later confirmed that this lesion was colon carcinoma. Arrows indicate lesion sites.

FIG. 7 summarizes tissue and blood dosimetry results for 1 patient infected with control antibody $^{131}$I-TA99, specific antibody $^{125}$I-AS 33 and $^{99m}$Tc HSA (for blood flow analysis). The large differences in tissue (tumor/liver) and blood (tumor/plasma) uptake ratios between AS 33 and control antibody demonstrate that localization is specific.

DETAILED DESCRIPTION OF THE INVENTION

Figure 4:
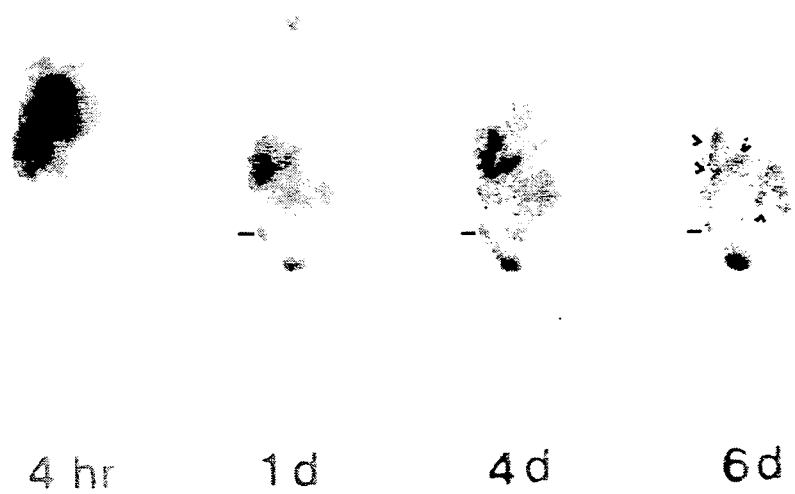
FIG. 4 shows gamma camera imaging results at 4 h, day 1, day 4 and day 6 using $^{131}$I labeled AS 33. At 24 hrs a primary colon cancer can be identified in the right lower quadrant of the abdomen. As blood born $^{131}$I antibody is cleared (6 d) liver metastasis and lymph mode metastasis are seen. All these sites of disease were confirmed at surgery and biopsies demonstrated antibody localization to these lesions and that these lesions were colon carcinomas. Arrows indicates lesion sites.
Figure 6:
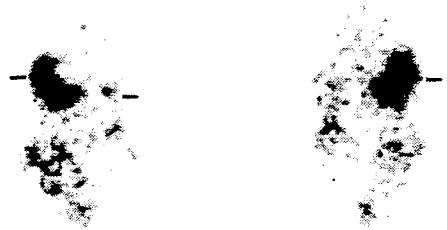
FIG. 6 illustrates gamma camera imaging results at 6 days using $^{131}$I labeled AS 33. $^{131}$I-AS 33 scan demonstrated a large mass in the right lobe of the liver. This was also identified on CTT. A smaller lesion is seen in the left lobe of the lesion which was not identified on CTT scan but was confirmed at surgery by biopsy. Arrows indicate lesion sites.

This invention provides a method of imaging a colorectal carcinoma lesion in a human patient which comprises administering to the patient a monoclonal antibody capable of binding to a cell surface antigen associated with the colorectal carcinoma lesion and which is labeled with an imaging agent under conditions so as to form a complex between the monoclonal antibody and the cell surface antigen, imaging any complex so formed, and thereby imaging the colorectal carcinoma lesion.

This method is useful in imaging primary colorectal carcinoma lesions and metastatic colorectal carcinoma lesions.

The monoclonal antibody designated AS 33 (A33) is a monoclonal antibody which is capable of binding to a cell surface antigen which is associated with colorectal carcinoma lesions and may be administered in an amount from about 0.01 mg to about 100 mg although an amount of monoclonal antibody from about 0.2 mg to about 50 mg is preferred. The monoclonal antibody of the invention may be administered by intravenous infusion.

This invention further provides a method of imaging a colorectal carcinoma lesion in a human patient wherein the monoclonal antibody AS 33 (HB 8779) is labeled with an imaging agent, such as $^{131}$I, and administered to the patient to bind to a cell surface antigen associated with a colorectal carcinoma lesion so as to form a complex between the monoclonal antibody AS 33 and the cell surface antigen, and thereby imaging colorectal carcinoma lesions.

This invention also provides the monoclonal antibody AS 33 labeled with a radioisotope imaging agent.

This invention further provides the monoclonal antibody AS 33 labeled with the imaging agent $^{131}$I.

This invention also provides a method of imaging a colorectal carcinoma lesion wherein the monoclonal antibody AS 33 is labeled with $^{131}$I and the amount of $^{131}$I -AS 33 administered to the patient is from about 0.1 mCi to about 50.0 mCi, although an amount of $^{131}$I from about 2.0 mCi to about 5.0 mCi is preferred.

This invention also provides a method of detecting a colorectal carcinoma lesion wherein the monoclonal antibody AS 33 labeled with an imaging agent is administered in an amount from about 0.01 mg to about 100 mg, although an amount of about 0.2 mg to about 50 mg is preferred.

Imaging of the complex comprising the labeled monoclonal antibody AS 33 (HB 8779) and the cell surface antigen associated with a colorectal carcinoma lesion may be carried out using a gamma camera or using single photon emission computed tomography.

This invention also provides a monoclonal antibody AS 33 (ATCC Accession number HB 8779) and the hybridoma cell line which produces it.

This invention also provides the monoclonal antibody AS 33 (HB 8779) and the hybridoma all line which produces it.

This invention further provides monoclonal antibody labeled with an imaging agent. The imaging agent may comprise the radioisotope $^{131}$I.

This invention also provides a method of imaging a colorectal carcinoma lesion wherein the amount of $^{131}$I labeled AS 33 administered is in an amount from about 0.1 mCi to about 50.0 mCi, although an amount from about 2.0 mCi to about 5.0 mCi is preferred.

This invention further provides a composition comprising an effective imaging amount of the monoclonal antibody AS 33 labeled with an imaging agent and a pharmaceutically acceptable carrier.

MATERIALS AND METHOD

Tissue Culture: Cultured human colon cancer cell lines were obtained from the Human Cancer Immunology Tumor Bank (Sloan-Kettering Institute, New York). Cultures were maintained as reported previously (2).

Production of Mouse mAb: BALB/c mice were immunized with (cultured pancreas carcinoma cells (ASPC-1). Subcutaneous and intraperitoneal injections of $1 \times 10^7$ cells were given three to ten times at intervals of 2 weeks. Three days after the last injection immune spleen cells were fused with mouse myeloma MOPC-21 NS/1 cells as described (3). Culture supernatants were tested for reactivity with a panel of cell lines derived from colon cancer and other tumor types using the anti-mouse Ig mixed hemabsorption assay (MHA) or protein A assay (PA). After three or more steps of subcloning, hybridoma cells were injected subcutaneously into nu/nu mice, (Swiss background) and sera from tumor-bearing mice were collected and used for serological, immunopathological and biochemical studies. In general, these methods have been described previously (2, 3).

Serological Procedures: The MHA assay for detecting antigens on cultured cells using rabbit anti-mouse IG and mouse anti-sheep red blood cells has been described (2, 3). Absorption tests, assessment of heat stability, proteinase sensitivity and antibody subclass determination were also performed as described (2-5). The reactivity of the antibodies with short term cultures of colonic tumors and normal colonic tissues was performed as described previously in co-pending patent application U.S. Ser. No. 118,411 (now abandoned), filed Nov. 6, 1987, continuation of U.S. Ser. No. 724,991, filed Apr. 19, 1985 (now abandoned).

Immunohistochemistry: Fresh frozen tissue sections were assayed for reactivity with mouse mAbs using fluorescein-conjugated goat anti-mouse Ig (Cappel Laboratories, Cochranville, Pa.) as described (6) Immunoperoxidase staining, using mAbs and peroxidase-conjugated goat anti-mouse Ig and 3-amino-9-ethylcarbazol (Histoset, Ortho Diagnostic System) was carried out following procedures recommended by the manufacturer.

Monoclonal AS 33 Ascites Production

General procedures: Nude mice are from MSKCC colony. Mice are purchased from The Jackson Laboratory, Bar Harbor, Me. Animal rooms are monitored for the presence of viruses. Cells and ascites must be bacteria-, fungus-, and myco-plasma-free. Ascites are screened for murine viruses before purification. Sterile procedures are used throughout production and purification procedures. A test for sodium azide is performed on chromatography columns prior to use. Quality and safety tests are performed on all final products.

Ascites production

1. Female nu/nu mice (2-3), primed with pristane oil, are injected intraperitoneally with $3-5 \times 10^6$ hybridoma cells (Passage 1).

2. When tumor is established, individual ascites are collected from injected mice, and antibody titers determined. Ascites cells are frozen and inoculated intraperitoneally into pristane-primed, irradiated male or female C3$^y$B$^6$F$^1$ hybrid mice (Passage 2).

3. Passage 2 ascites cells are injected into 75-100 pristane-primed, irradiated F$^1$ male or female mice (passage 3). Donor cells are pooled according to donor's titer; cells not needed for injection are stored frozen.

4. The same procedure is repeated with Passage 4 ascites cells, and continued serially until antibody titers decrease.

5. Backup frozen cells and 3 and 4 are used to increase the ascites pool, and frozen cells from Passages 1 and 2 are used to institute the procedure.

6. A final batch of 2-3 liters is established, the antibody titer determined, and a sample tested for contamination with murine viruses.

METHOD FOR PURIFICATION OF MONOCLONAL ANTIBODY AS 33

Buffers:

Buffer A—0.03 M HEPES/NaOH, PH 8.0
Buffer B—0.5 M HEPES/NaOH, pH 8.0
Buffer C—0.03 M HEPES/NaOH, pH 8.0
Buffer D—0.05 M Phosphate/NaOH, 0.15 M NaCl, pH 7.0
Saturated Ammonium Sulfate The buffers are prepared with water for injection, USP and filtered through 0.22 uM filters. No preservatives are used in any of the buffers with the exception of those buffers used for column storage, to which sodium azide is added to a final concentration of 0.02%.

All glassware, tubing and other apparatus are steam, dry heat or gas sterilized. Unless otherwise stated, all procedures are carried out at 2° C. to 8° C.

Procedure

Lipoproteins are removed from ascites by centrifugation at $135,000 \times G$ for 3 hours, and the material is stored in quantities suitable for purification.

Antibody is purified using the following steps:
1. Ammonium sulfate precipitation 0%–45%; pH is maintained at pH 7.4 10 NaOH.
2. After equilibration of for 60 min., the suspension is pelleted by centrifugation at $10,000 \times G$ for 15 min.
3. The pellet is dissolved in a small volume of Buffer A and centrifuged at $2000 \times G$.
4. The supernatant from step 3 is applied to a Sephadex G50 superfine column ($5 \times 42$ cm), equilibrated with Buffer A, at a flow rate of 25 ml/min at room temperature.
5. The eluted protein fraction is applied to a S-Sepharose Fast Flow Column ($5 \times 10$ cm), equilibrated with Buffer A, at a flow rate of 35 ml/min at room temperature.
6. After the protein elution curve returns to baseline, the running buffer is changed to 93% Buffer A and 7% Buffer B.
7. After the protein elution curve returns to baseline, the running buffer is changed to 93% Buffer A and 7% Buffer B.
8. The protein eluted after running 100% Buffer C is applied to a Sephadex G50 superfine column ($5 \times 42$ cm), equilibrated with buffer D, at a flow rate of 25 ml/min.
9. The eluted protein is sterilized by filtration, vialed and frozen. This is the A33 final product.

EXPERIMENTAL RESULTS

From 23 fusions of immune splenocytes with NS/1 myeloma cells, 4 antibody-producing clones with a restricted pattern of reactivity with cultured cell lines were selected for detailed analysis. These antibodies were found to be unreactive with A, B, H, $Le^a$, $Le^b$, X, Y and I specific glycoproteins. The serological specificity of these antibodies was determined on a panel of 154 established human cancer cell lines, on 10 short-term cultures of human fibroblast and kidney epithelial cells and on a panel of short-term cultures of normal colon benign and malignant colon tumors. The reactivity of these antibodies with a panel of normal human fetal and adult tissues, as well as normal colon epithelium and colon cancer tissues from 55 patients, was examined using indirect immunofluororescence and the ABC immunoperoxidase techniques.

AA 33

Monoclonal antibody AS 33 reacted with 5/17 colon carcinoma and ⅓ pancreatic carcinoma cell lines with a titer of $10^3$–$10^6$ AS 33 was also reactive with 3/5 T leukemia cell lines but all other tumor cell types tested were unreactive (See FIG. 1).

Reactivity of T-cell leukemias with monoclonal antibody AS 33 did not correlate with expression of other T-cell related antigens, including those detected by OKT4, OKT6, OKT11, T37, CL3-3 and CL3-40.

In tissues, reactivity of monoclonal antibody AS 33 was restricted to carcinoma tissue and normal colonic mucosa in the majority of cases of colon cancer studied (50/59) including primary tumors and liver metastases. AS 33 reactivity was observed in all cases in 90 to 100% of tumor cells. Reactivity was strong and homogenous.

AS 33 also showed a very strong cytoplasmic reactivity in all samples of normal colonic mucosa, including samples of ascending, transverse and descending colon. Other normal tissues which showed AS 33 antigen expression were the ductiles of the major salivary glands and positive but heterogenous reaction in the ducts and acini of the normal breast (See FIG. 2).

Other normal tissues tested including liver, kidney, lung, stomach, bladder, cervix uteri, ovary, larynx and adrenal gland were negative (See FIG. 2).

Other carcinomas tested showed ± reactivity in an infiltrating duct carcinoma of breast scattered positive cells were seen in a renal cell carcinoma and 4 gastric carcinomas for AS 33.

The antigen detected by monoclonal antibody AS 33 was not destroyed by heating at 100° C. for 5 minutes and it was weakly detectable in choloroform/methanol extracts of ASPC-1 cells.

Imaging Experiments

The monoclonal antibody AS 33 can be labeled with $^{131}I$ by the chloramine-T method and retains 50–70% of its immunoreactivity as tested by sequential quantitative absorption assays.

Labeling of Purified AS 33 with $^{131}I$

Sterile technique and pyrogen-free glassware were used in all labeling steps. About 0.2 to about 25.0 mg of AS 33 is added to 0.5 ml of 0.15 M NaCl/0.05 M $H_3PO_4$, pH 7.5. The antibody is iodinated with 5 mCi $^{131}I$ as NaI and 50 microliters of chloramine-T (10 mg/ml) for 30 sec at 24° C. The reaction is stopped by addition of 50 mCi sodium metabisulfate (12 mg/ml) and transferred to a 25 ml Biogel P30 column (50–100 mesh). Fractions with the highest amount of radioactivity are pooled and filtered through a 0.2 micron filter. Using similar techniques, AS 33 also was labeled with 2 mCi $^{125}I$ for use in six patients who received both mAbs, AS 33 and control TA99. Monoclonal antibody TA99 was labeled as described above with 5 mCi $^{131}I$.

Administration of $^{131}I$ AS 33

The uptake of $^{131}I$ in the thyroid was blocked by Lugol's solution; 5 drops po bid starting 24 h prior to antibody administration. $^{131}I$ AS 33 was administered in doses of about: 0.2 mg; 2 mg; 10 mg; and 25, by one hour intravenous infusion in about 100 to about 200 ml of saline/5% human serum albumin.

Fifteen patients, all with liver metastases and were scheduled to undergo surgery were administered $^{131}I$ labeled AS 33. $^{131}I$-AS 33 was administered intravenously at 5 dose levels (0.2 mg, 2 mg, 10 mg, 25 mg and 50 mg), which was labeled with about 2.0 to about 5.0 mCi of $^{131}I$. Three patients were entered at each dose level.

Imaging Results

Evaluation included whole body imaging of $^{131}$I-AS 33 using a gamma camera (daily, day 1-8); blood flow study using $^{99m}$Tc-albumin liver/spleen scan, CTT scan, hepatic arteriogram (once during the week of imaging); blood pharmacokinetics (day 1-8); a biopsy of tumors and normal tissues (day 8). Fifteen patients were entered, and 12 patients were evaluated. Antibody localization to tumor was documented by external imaging and radioactive tissue counting in all but one patient. Examination of the resected tumor specimens revealed that most of the radioisotope was localized in the rim of viable tumor tissue surrounding the large necrotic centers typical for these metastatic lesions. The maximal tumor: liver ratio ranged from 6.9.1 to 100.1:1, except for the patient whose liver metastases could not be visualized by external imaging; in this case the ratio was 2.7:1. In three patients with extra hepatic sites of disease (primary/recurrent colon tumors, lymph node metastases or lung metastases) antibody localization to tumor tissue was also seen. At the highest dose level administered so far (25 mg), imaging of liver metastases or lung metastases) antibody localization to tumor tissue was also seen. Also at the highest does level administered so far (25 mg), imaging of liver metastases was more distinct that at lower dose levels. This difference is not explained by retention of a higher proportion of the injected does in tumor tissue which was $0.9 - 15.0 \times 10^{-3}$ per gram over the entire dose range. Rather, blood clearance of $^{131}$I-AS 33 was found to be more rapid at the highest dose level, resulting in tumor: plasma ratio of 13.0-17.8 on day 8 in the three patients receiving the 25 mg dose as opposed to ratios of 4.1 to 11.3 in patients treated at the lower does levels.

FIG. 3 summarizes tissue and blood dosimetry data collected from the twelve patients at day 7-8 who were administered $^{131}$I labeled AS 33.

Other imaging agents which are well known to those skilled in the art are useful in the practice of this invention. Other such agents include, but are not limited to the radioisotopes: $^{124}$I; $^{123}$I; $^{99}$Tc; and $^{111}$In.

Additionally, other methods of imaging the complex comprising radiolabeled antibody and cell surface antigen associated with colorectal carcinoma may be used. Other such methods include, but are not limited to single photon emission computed tomography (SPECT) and positron emission tomograph (PET).

The method of this invention also may be used as a therapy in the treatment of colorectal carcinomas, i.e., as a method of delivering radioisotopes to the colorectal carcinoma lesion.

The hybridomas which produce the monoclonal antibodies designated AS 33 and TA99 have been deposited with the American Type Culture Collection in Rockville, Md., U.S.A. 20852, and identified by ATCC Accession Nos. HB 8779 and HB 8704, respectively. These deposits were made pursuant to the provisions of the Budapest Treaty on the International Recognition of the Deposit of Microorganisms For The Purposes of Procedure (Budapest Treaty).

What is claimed is:

1. The monoclonal antibody AS 33 (HB 8779).
2. The hybridoma cell line which produces the monoclonal antibody of claim 1.
3. The monoclonal antibody of claim 1, labeled with an imaging agent.
4. The monoclonal antibody of claim 3, wherein the imaging agent comprises a radioisotope imaging agent.
5. The monoclonal antibody of claim 4, wherein the radioisotope comprises $^{131}$I.
6. The monoclonal antibody of claim 5, wherein the amount of $^{131}$I is from about 0.1 mCi to about 50.0 mCi.
7. The monoclonal antibody of claim 6, wherein the amount of $^{131}$I is from about 2.0 mCi to about 5.0 mCi.
8. A composition comprising an effective imaging amount of the monoclonal antibody of claim 1 and a pharmaceutically acceptable carrier.

* * * * *